United States Patent [19]

Ylvisaker

[11] Patent Number: 4,473,913

[45] Date of Patent: Oct. 2, 1984

[54] THERAPEUTIC SUPPORT CUSHION

[76] Inventor: Carl J. Ylvisaker, 213 E. 10th, McMinnville, Oreg. 97128

[21] Appl. No.: 383,711

[22] Filed: Jun. 1, 1982

[51] Int. Cl.³ .............................................. A47G 9/00
[52] U.S. Cl. .......................................... 5/435; 5/436; 5/441; 5/465; 5/443
[58] Field of Search .................... 5/431, 432, 434–437, 5/443, 465, 440, 446

[56] References Cited

U.S. PATENT DOCUMENTS

| | | | |
|---|---|---|---|
| 1,710,400 | 4/1929 | Bebout | 5/465 |
| 2,688,142 | 9/1954 | Jensen | 5/435 |
| 2,958,323 | 11/1960 | Behrens | 5/440 |
| 3,009,172 | 11/1961 | Eidam | 5/436 |
| 3,378,861 | 4/1968 | Lousberg | 5/432 |
| 3,747,916 | 7/1973 | Benson | 5/435 |
| 3,926,181 | 12/1975 | Eischen, Jr. | 5/436 |
| 4,118,813 | 10/1978 | Armstrong | 5/435 |
| 4,171,549 | 10/1979 | Morrell et al. | 5/465 |
| 4,207,635 | 6/1980 | Leroy | 5/437 |

FOREIGN PATENT DOCUMENTS

| | | | |
|---|---|---|---|
| 1065909 | 4/1967 | United Kingdom | 5/446 |
| 1199533 | 9/1970 | United Kingdom | 5/435 |

Primary Examiner—Alexander Grosz
Assistant Examiner—Michael F. Trettel
Attorney, Agent, or Firm—Kolisch, Hartwell, Dickinson & Anderson

[57] ABSTRACT

An elongate cushion for therapeutically supporting a person in an arched face-down prone position. The cushion has an upper surface which slopes upwardly from each end toward the middle. At least one end has a channel the sides of which support a person's head placed face-down therein, with the channel serving as an unobstructed air passageway. The preferred embodiment consists of an assembly of three nestable pillows. Two end pillows, each having a channel, support an intermediate pillow. Also, the end pillows are sized so that, when spaced apart, they will, in cooperation with a horizontal support surface on which they are placed, support a person in a supine position.

4 Claims, 3 Drawing Figures

THERAPEUTIC SUPPORT CUSHION

BACKGROUND AND SUMMARY OF THE INVENTION

This invention pertains to a therapeutic cushion for supporting a person in a face-down prone position. More specifically, it pertains to such a cushion which has a channel in one end which provides an air passageway for a person's head placed face-down therein. It also pertains to such a cushion which is formed of an assembly of nestable pillows which alternatively support a person in a supine position.

The present invention is intended for professional use in therapy, orthopedic, chiropractic and similar centers and for individual use for positioning a person so that his or her back is in a forwardly curving condition. Typically, when a person is placed on a cushion which is high in the center and low at the ends, with the abdomen being placed on the high, center region, the spine is completely flexed except for the cervical region. The reason for this exception is that in order for a person to lay comfortably on a conventional cushion having a completely smooth surface, he or she must either turn his or her head sideways or support the forehead with an additional pillow. These positions cause the cervical region of the spine to either be twisted or bent in an undesirable manner. It is therapeutically preferable to have a person's entire spine in a curved, relaxed condition. This is also important where a doctor is providing treatment or performing ultrasound or other techniques on the person.

In a similar fashion, it is also desirable, as part of the treatment program, to have a person lay down in what has been termed in the trade, a Fowler position. This is a supine position in which the knees are bent and the shoulders and neck are flexed so that the entire spine is completely flexed. In this position the spinal joints are opened and pressure is taken off of nerve roots.

It is therefore a desired object of this invention to provide a cushion which will completely support a person in a face-down prone position. This includes structure which will support the head of a person so that the entire spine remains in a completely flexed condition while allowing such a person to have an unobstructed breathing passageway.

It is also a desired objective to provide such a cushion which is formed of an assembly of pillows which may be disassembled and easily transported.

It is a further objective to provide such an assembly of pillows which may be used in both a face-down prone and a Fowler-type supine position.

Another object of this invention is to provide an assembly which will hold itself in an assembled position when placed and used on a support surface.

It is also a desire to provide a cushion having adjustable resilience to meet the needs of different users.

A preferred embodiment of this invention includes an assembly having two end pillows which have a generally V-shaped profile when viewed from the side and are placeable against each other to form a valley. An intermediate pillow having a diamond-shape when viewed from the side, is nestable in the valley to complete the assembled cushion. A channel disposed in at least one of the end pillows has an opening in an upper surface sized to support the sides of a head placed face-down thereon. The channel also provides a clear air passageway.

The two end pillows also support a person in a Fowler-type supine position when they are spaced apart from their positions in the three-pillow assembly.

It has been found that by making the pillows inflatable and putting conventional air-lock valves on them, their firmness or resilience may be varied to satisfy the needs of different persons. In addition, it is more easily transported in a deflated condition. Also, by mounting soft rubber pads near the corners of the bottom surface of each end pillow, the pillows tend to grip a surface on which they are placed, thereby preventing their slipping apart during use.

These and additional objects and advantages of the present invention will be more clearly understood from a consideration of the drawings and the following detailed description of the preferred embodiments.

DETAILED DESCRIPTION OF THE INVENTION

Figure 1:
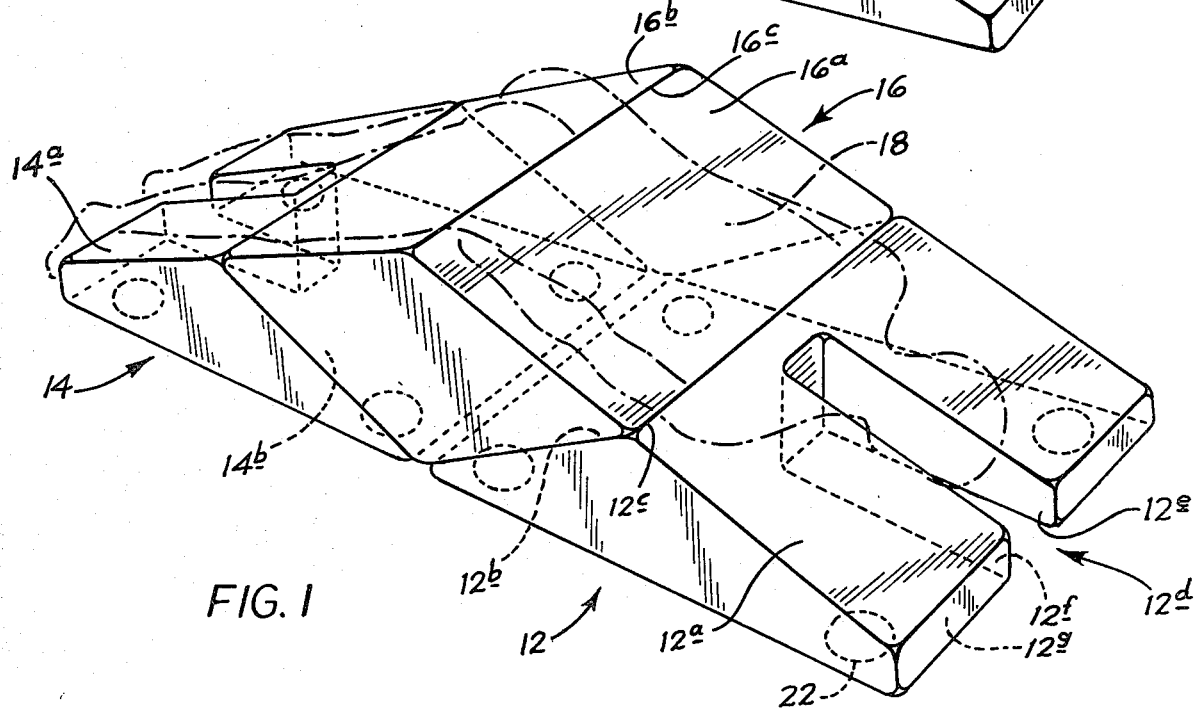
FIG. 1 is a perspective view of a first preferred embodiment showing a cushion formed of an assembly of pillows assembled for use by a person in a face-down prone position.

Referring to FIG. 1 and describing a first preferred embodiment of this invention, a cushion, shown generally at 10 is formed of a nestable assembly of end pillows 12, 14 and intermediate pillow 16. As can be seen, cushion 10 has an overall form which is long enough to support essentially the entire length of a person 18, shown in dash-dot lines, in a face-down prone position.

Each pillow is made of a resilient foam rubber material, as is conventionally used for cushions, which is covered with a protective material such as vinyl or other fabric. End pillows 12, 14 are constructed identically. It will therefore be understood that in discussing the structure of pillow 12, that similar comments are appropriate for pillow 14.

Pillow 12 has a pair of inclined upper surfaces 12a, 12b which have a generally rectangular outline and which slope upwardly toward each other from opposite ends of the pillow to a common horizontal upper ridge 12c. It can be seen in the assembly of FIG. 1 that upper surface 12a is exposed while upper surface 12b is covered by pillow 16. Disposed in the portion of pillow 12 associated with and opening into upper surface 12a is a channel 12d, also referred to herein as channel-defining means. The channel includes parallel walls 12e, 12f which extend through the bottom of pillow 12 and extend generally perpendicularly with respect to ridge 12c. It has been found that a separation between walls 12e, 12f of approximately four inches is adequate to support a head placed face-down thereagainst while allowing unobstructed air passage through the channel for breathing.

Intermediate pillow 16 is essentially diamond-shaped as viewed from the side. It also has upper surfaces 16a, 16b which are rectangular and inclined so that they slope upward to a common horizontal ridge 16c when assembled with pillows 12, 14 as shown in FIG. 1. Pillow 16 is structured so that its upper surfaces are coplanar with the exposed upper surfaces of the end pillows as shown. This provides an elongate cushion 10 having upper surfaces which are generally rectangular in outline and slope upwardly from the ends to a common central ridge which is ridge 16c.

Each end pillow has a bottom planar surface, such as surface 12g. Fixedly attached adjacent each corner of bottom surface 12g is a generally planar resilient rubber pad, such as pad 22, which is attached to the bottom surface by rubber cement or other similar adhesive.

Figure 3:
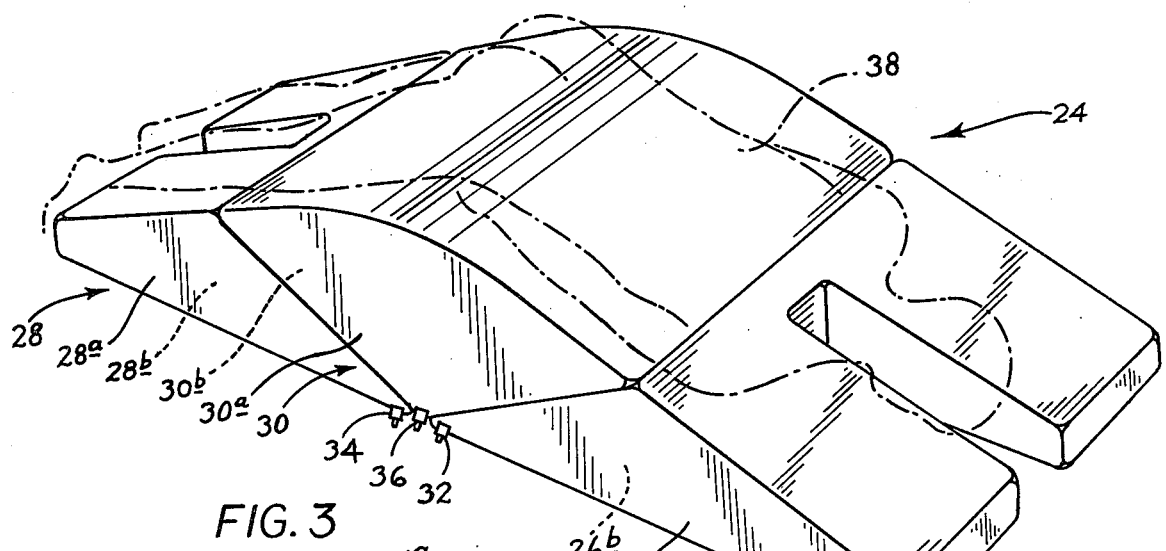
FIG. 3 is a perspective view similar to FIG. 1 of a second preferred embodiment showing an assembly having inflatable pillows one of which is only partially inflated.

Referring now to FIG. 3, and describing a second preferred embodiment of the present invention, a cushion, shown generally at 24, is formed of an assembly of end pillows 26, 28 and intermediate pillow 30. These pillows are inflatable and are constructed to have the same geometrical proportions as those described for pillows 12, 14, 16 when in a fully inflated condition. Pillows 26, 28, 30 have outer shells 26a, 28a, 30a, respectively, which contain plenums 26b, 28b, 30b, respectively, when inflated. Pillow 30 has an upper ridge 30c which also forms the upper ridge of cushion 24. Pressure within the plenums are controlled by valves 32, 34, 36 which are attached to shells 26a, 28a, 30a, respectively. These valves, also referred to herein as resilience-adjusting means and valve means, may be manually opened or closed to allow for inflating or deflating the pillows. FIG. 3 shows pillows 26, 28 fully inflated. Pillow 30, being less than fully inflated, has an upper ridge which is lower than when fully inflated. This makes it softer for a person 38 lying on it. Other persons may prefer a very firm cushion which is obtainable by increasing the pressure inside the pillows.

During use as a support for a person in a face-down prone position, the pillows are assembled as shown in FIGS. 1 or 3, the inflatable pillows having been inflated first. The end pillows nearly touch to form a valley in which the intermediate pillow nests. This leaves the channels exposed.

A cushion made of foam, as was described for the embodiment shown in FIG. 1, has a fixed resiliency. If a person desires a cushion with a lower height or one which is softer or harder, then an inflatable cushion should be used. The cushion shown in FIG. 3 is inflatable with intermediate pillow 30 slightly deflated so that it has a more rounded and lower maximum height when a person is lying on it.

When a person lies on cushion 10 or 24, he or she should place his or her abdomen on top of the upper ridge located on the top of the intermediate pillow. The feet are then placed adjacent one end of the cushion with the legs in a straight but relaxed condition. The person then places his or her face down into the channel on the opposite end. The channel is narrow enough to support the head while allowing for unobstructed passage of air through the channel during breathing. Thus, the person can lie with a continuously curved and flexed spine.

It should be apparent from viewing FIGS. 1 and 3 that the intermediate pillow tends to apply an outwardly directed force on the end pillows when pressure is applied to the top of it, as when person is lying on it. Outward movement is prevented by the use of what is termed means for holding the pillows in the assembled, operative position. The preferred way of doing this is to use what is also termed herein as surface-gripping means, such as pads 22 fixed to the bottom surfaces of the end pillows. The friction provided by these pads against a surface on which the pillows are placed prevents them from sliding apart.

Figure 2:
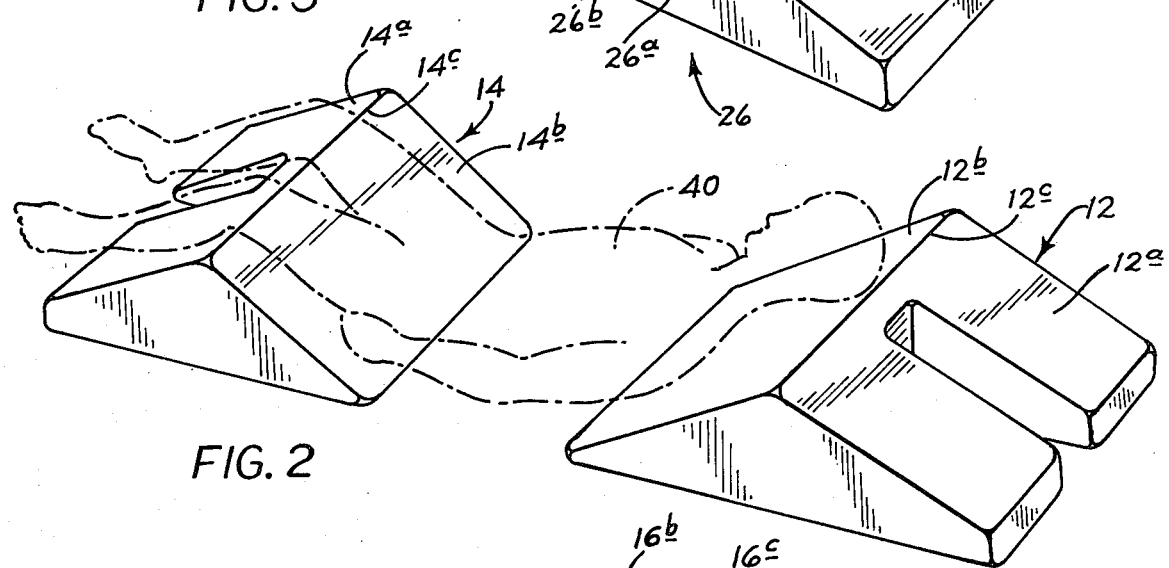
FIG. 2 is a perspective view of two of the pillows of the assembly of FIG. 1 in operative position for use by a person in a Fowler-type supine position.

Referring to FIG. 2, it is also therapeutically desirable to have a person 40 lie in a Fowler-type supine position. In this position, the spine is curved, including the cervical region, and the legs are bent with the knees supported in an elevated position. End pillows 12, 14 are constructed so that when placed in a slightly spaced apart position with the end pillows having the same relative orientation as they do in the three-pillow cushion as shown, they assist person 40 in lying in this position. The hips are located against the lower edge of normally unexposed upper surface 14b of end pillow 14 with the knees located above top ridge 14c and the lower legs lying on upper surface 14a. End pillow 12 is then placed so that the lower edge of surface 12b is just under the person's shoulders with the head lying just below the ridge, as shown. This provides for a continuous curvature of the back. Pillows 26, 28 may, of course, be used the same way.

It can be seen that the assembly consisting of two end pillows with channels in them plus an intermediate pillow accommodates the positioning of a person in a face-down prone position. Additionally, the two end pillows, when placed properly apart from each other, accommodate a person lying in a Fowler-type supine position. The one assembly can therefore be used to accommodate the positioning of a person in both positions and is readily transportable because of the reduced size of the individual pillows making up the cushions. Also, by using inflatable pillows, the resilience of the cushion can be adjusted for each individual user's characteristics and preference. The inflatable embodiment is even more portable than the foam-filled embodiment because of the substantially reduced size it has when deflated.

The use of rubber pads on the bottom surfaces of the end pillows also assures that they will stay in the desired operative positions during use.

While the invention has been particularly shown and described with reference to the foregoing preferred embodiments, it will be understood by those skilled in the art that other changes in form and detail may be made therein without departing from the spirit and scope of the invention as defined in the following claims.

It is claimed and desired to secure by Letters Patent:

1. An assembly of therapeutic resilient pillows operatively placeable on a generally horizontal support surface for supporting a person in an arched face-down prone position, said assembly comprising
    a pair of end pillows, each pillow having a generally planar bottom surface, and a pair of generally oppositely inclined generally rectangular planar upper surfaces sloping in predetermined directions, facing upwardly away from each other and having a common generally horizontal upper ridge, said end pillows being placeable, in operative position, adjacent each other in such a manner that each end pillow has one of said upper surfaces facing inward toward the other end pillow to form, in combination, a valley,
    an intermediate pillow nestable in said valley and having, when nested therein, a pair of generally oppositely inclined generally rectangular upper surfaces facing upwardly away from each other and having a common generally horizontal upper ridge, said pillows forming, when assembled in operative position, an elongate cushion having a generally planar horizontal bottom surface and a pair of generally oppositely inclined generally rectangular upper surfaces facing upwardly away from each other and having a common generally horizontal upper ridge, and means defining a channel in at least one of said end pillows, which channel opens through the upper surface facing outwardly away from the other end pillow when said pillows are in operative position, said means including walls defining said channel appropriately spaced apart to support the head of a person whose face is placed in said channel, said channel forming an unobstructed air passageway from such a face to air surrounding said pillow.

2. The assembly of claim 1 wherein said head-supporting channel walls extend generally normal to the ridge of each end pillow having said means defining a channel.

3. An assembly of therapeutic resilient pillows operatively placeable on a generally horizontal support surface for supporting a person in an arched face-down prone position, said assembly comprising a pair of end pillows, each pillow having a generally planar bottom surface, and a pair of generally oppositely inclined upper surfaces facing upwardly away from each other and joining at a common upper ridge, said end pillows being placeable, in operative position, adjacent each other in such a manner that each end pillow has one of said upper surfaces facing inward toward the other end pillow to form, in combination, a valley, and an intermediate pillow nestable in said valley and having, when nested therein, a pair of generally oppositely inclined upper surfaces facing upwardly away from each other and joining at a common upper ridge, said pillows forming, when assembled in operative position, an elongate cushion having a generally planar horizontal bottom surface and a pair of generally oppositely inclined upper surfaces facing upwardly away from each other and joining at a common upper ridge.

4. An assembly of therapeutic resilient pillows operatively placeable on a generally horizontal support surface for supporting a person alternatively in an arched face-down prone position or in a supine position, said assembly comprising a pair of end pillows, each pillow having a generally planar bottom surface and a pair of generally oppositely inclined upper surfaces facing upwardly away from each other and joining at a common upper ridge, said end pillows being placeable, in operative position, adjacent each other in such a manner that each end pillow has one of said upper surfaces facing inward toward the other end pillow to form, in combination, a valley, and an intermediate pillow nestable in said valley and having, when nested therein, a pair of generally oppositely inclined upper surfaces facing upwardly away from each other and joining at a common upper ridge, said end pillows forming, when assembled in operative position with said intermediate pillow nested in the valley formed by the end pillows, an elongate cushion having a generally planar horizontal bottom surface and a pair of generally oppositely inclined upper surfaces facing upwardly away from each other and joining at a common upper ridge, said end pillows further being capable of forming, when generally assembled without the intermediate pillow in relative orientation corresponding with the orientation of said end pillows in operative position, an assembly capable of supporting a person in a supine position with one of said end pillows supporting the person's legs with the knees superposed the upper ridge of said end pillow and the other end pillow supporting at least a portion of the person's torso.

* * * * *